(12) United States Patent
Rosignoli

(10) Patent No.: US 11,235,010 B2
(45) Date of Patent: Feb. 1, 2022

(54) COMPOSITION CONTAINING LACTIC ACID BACTERIA AND ITS USE TO TREAT ATOPIC DERMATITIS

(71) Applicant: GALDERMA RESEARCH & DEVELOPMENT, Biot (FR)

(72) Inventor: Carine Rosignoli, Mougins (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 791 days.

(21) Appl. No.: 15/766,309

(22) PCT Filed: Oct. 7, 2016

(86) PCT No.: PCT/EP2016/074065
§ 371 (c)(1),
(2) Date: Apr. 5, 2018

(87) PCT Pub. No.: WO2017/060468
PCT Pub. Date: Apr. 13, 2017

(65) Prior Publication Data
US 2018/0289754 A1    Oct. 11, 2018

Related U.S. Application Data

(60) Provisional application No. 62/238,244, filed on Oct. 7, 2015, provisional application No. 62/340,266, filed on May 23, 2016.

(51) Int. Cl.
| | | |
|---|---|---|
| *A61K 35/00* | (2006.01) | |
| *A61K 35/747* | (2015.01) | |
| *A61P 17/00* | (2006.01) | |
| *A61K 35/745* | (2015.01) | |
| *A61K 9/00* | (2006.01) | |
| *A61K 9/06* | (2006.01) | |
| *A61K 9/08* | (2006.01) | |
| *A61K 47/18* | (2017.01) | |
| *A61K 47/10* | (2017.01) | |
| *A61K 47/44* | (2017.01) | |
| *A61P 17/04* | (2006.01) | |

(52) U.S. Cl.
CPC .......... *A61K 35/747* (2013.01); *A61K 9/0014* (2013.01); *A61K 9/06* (2013.01); *A61K 9/08* (2013.01); *A61K 35/745* (2013.01); *A61K 47/10* (2013.01); *A61K 47/183* (2013.01); *A61K 47/44* (2013.01); *A61P 17/04* (2018.01); *A61K 2035/115* (2013.01)

(58) Field of Classification Search
CPC ...... A61K 35/745; A61K 9/08; A61K 9/0014; A61K 47/44; A61K 2035/115; A61K 47/183; A61K 47/10; A61K 35/747; A61K 9/06; A61P 17/04
See application file for complete search history.

(56) References Cited

U.S. PATENT DOCUMENTS

| | | |
|---|---|---|
| 2006/0171936 A1 | 8/2006 | Gueniche et al. |
| 2014/0079677 A1 | 3/2014 | Baur et al. |

FOREIGN PATENT DOCUMENTS

| | | |
|---|---|---|
| EP | 1736537 A1 | 12/2006 |
| EP | 2397145 A1 | 12/2011 |
| EP | 2796142 A1 | 10/2014 |
| WO | 03/070203 A1 | 8/2003 |
| WO | 2010/130662 A1 | 11/2010 |
| WO | 2012/071654 A1 | 6/2012 |

OTHER PUBLICATIONS

International Search Report and Written Opinion of the International Searching Authority dated Dec. 5, 2016 corresponding to International Patent Application No. PCT/EP2016/074065, 15 pages.
Tanaka, A., "Prophylactic effect of oral administration of Latctobacillus johnsonii NCC533 (La1) during the weaning period on atopic dermatitis in NC/NgaTnd mice," European Journal of Dermatology, vol. 18, No. 2, Mar. 2008, pp. 136-140, XP009185116.
Inoue, R. et al., "Oral treatment with probiotic Latctobacillus johnsonii NCC533 (La1) for a specific part of the weaning period prevents the development of atopic dermatitis induced after maturation in model mice, NC/Nga," British Journal of Dermatology, vol. 156, No. 3, Mar. 2007, pp. 499-509, XP002521659.

*Primary Examiner* — Satyendra K Singh
(74) *Attorney, Agent, or Firm* — Foley & Lardner LLP; Sunit Talapatra

(57) ABSTRACT

A composition is described that includes at least one lactic acid bacteria, preferably *Lactobacillus johnsonii* LA1 NCC 533 (deposit number CNCM I-1225) in an acceptable carrier. Also described, is use of the composition in the treatment and/or prevention of a dermatological disease, preferably atopic dermatitis.

8 Claims, 5 Drawing Sheets

Figure 1:
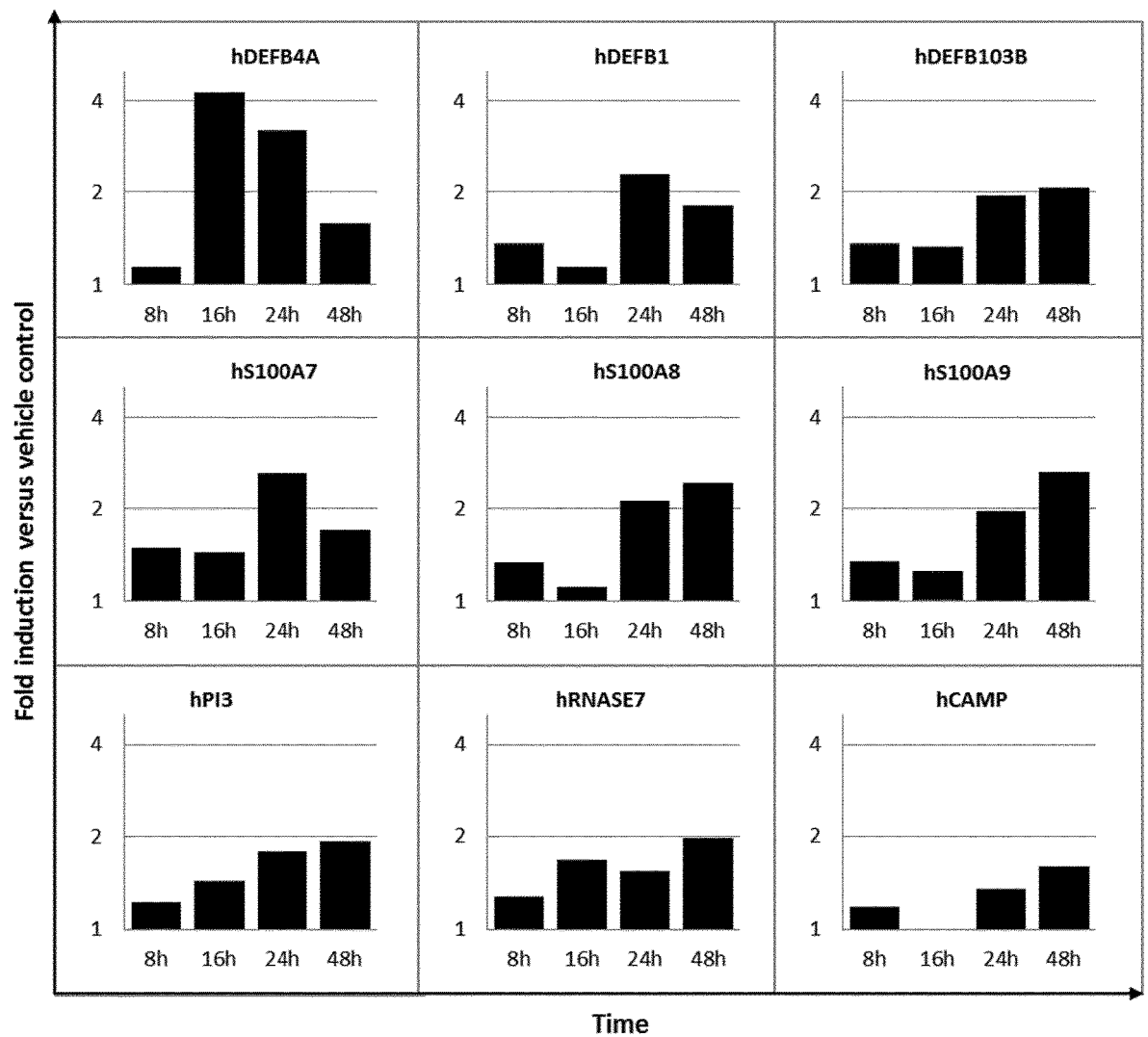

COMPOSITION CONTAINING LACTIC ACID BACTERIA AND ITS USE TO TREAT ATOPIC DERMATITIS

CROSS-REFERENCE TO PRIOR APPLICATIONS

This application is a National Stage of PCT/EP2016/074065 filed Oct. 7, 2016, and designating the United States (published on Apr. 13, 2017, as WO 2017/60468 A1), which claims priority under 35 U.S.C. § 119 to U.S. Provisional Application No. 62/238,244, filed Oct. 7, 2015, and U.S. Provisional Application No. 62/340,266, filed May 23, 2016, each hereby expressly incorporated by reference in its entirety and each assigned to the assignee hereof.

FIELD OF THE INVENTION

The present invention generally relates to dermatologic field and, more particularly relates to compositions for preventing and/or treating atopic dermatitis, in particular by boosting the endogenous antimicrobial defenses.

BACKGROUND OF THE INVENTION

Our environment is contaminated by a vast array of potentially pathogenic microorganisms. Skin keratinocytes, epithelial cells lining the gastrointestinal tract, respiratory tract, and genitourinary tract all provide a physical barrier that protect against microbial intrusion into the body. In addition, these epithelia contribute to the host defenses by producing and secreting antimicrobials to limit access of bacteria and other microorganisms. These antimicrobial molecules constitute key components of the basic defense line of the innate immunity.

Antimicrobial peptides (AMPs) are very important component of innate immunity. They act either directly, destroying bacteria, fungi and some viruses or indirectly, stimulating some elements of inflammatory and immune reactions. The AMPs are produced in human skin and involved in cutaneous defense including defensins, cathelicidin, dermcidin and many other proteins such as lysozyme, elastase, complement, RNase and S100 proteins. Altered expression of AMPs has been recognized in some skin diseases and appears to play a role in determining susceptibility of patients with skin disorders to pathogens. The expression and secretion of several AMPs such as hBD-2 (DEFB4A), hBD-3 (DEFB103), LL-37 (CAMP), RNase 7 and Psoriasin (S100A7), are induced in atopic dermatitis (AD) lesions skin compared with healthy controls. However, the levels of AMP expression and secretion are lower than those detected in psoriasis skin. These quantitative differences may explain the higher susceptibility of AD skin with infections especially by *S. aureus* compared to psoriasis skin.

Atopic dermatitis (AD) is a chronic, relapsing, inflammatory skin disease that affects up to 25% of children and 2% to 3% of adults. Around 60% of patients develop symptoms in their first year of life and 90% before their five years of age and the majority of affected children have spontaneous resolution of disease before adolescence. However, some people continue to suffer from AD into adulthood and only a small percentage first develops symptoms as adults.

Symptoms can vary but AD commonly starts with dry skin that is often very itchy. Scratching causes the dry skin to become red, swollen, scaly and irritated. Small bumps that open and ooze when scratched and crusts may develop. Over time, a recurring rash can lead to tough and thickened skin (lichenification). The location and distribution of symptoms may change with age but AD can typically affect the face, the neck, the insides of the elbows and/or the backs of the knees as well as the hands, the wrists and/or the feet. Even if the pathogenesis of AD is not completely understood, the disorder appears to result from complex interactions between genetic, immunologic and environmental factors. AD is characterized by a disturbed epidermal barrier leading to trans-epidermal water loss and subsequent dry skin and to increased penetration of allergens and microbes into the skin. This disruption of the epidermal barrier may be caused by genetic alterations such as mutations in the filaggrin gene, essential for the formation and hydration of the skin barrier. Moreover, atopic skin is deficient in ceramides (lipid molecules), toll like receptor 2 and antimicrobial peptides needed to defend against infectious agents, which may explain increased susceptibility to skin infections (often with *Staphylococcus aureus*). In AD patients, there is also an exacerbate immune response which is biased towards Th2 type response with resultant release of chemokines and pro-inflammatory cytokines such as IL-4, IL-13 or IL-31 that promote IgE production and inflammatory responses leading to pruritic inflammation of the skin. These cytokines also contribute to reduce filaggrin and antimicrobial peptide expression.

AD is a serious health concern and can significantly impair the quality of life of patients. Indeed, children or adults with AD may be affected by the social stigma of a visible skin condition but also by the intense itching characteristic of the disease which often leads to significant sleep disturbance in up to 60% of children with AD. Moreover, depression has been noted in both teens and adults affected with AD. This suggests the need to effectively manage this disease for patient's general well-being and quality of life.

The maintenance therapy for AD consists in hydrating the skin and maintaining a healthy skin barrier with the regular use of emollients. In case of exacerbation, topical corticosteroids remain the first-line therapy to reduce cutaneous inflammation both in children and adults. Topical calcineurin inhibitors are alternatives to the chronic use of topical corticosteroids in children older than 2 years. In adults with severe and recalcitrant AD, phototherapy or systemic immunosuppressive medications may be helpful. Oral or topical antibiotics can also be used to prevent or treat secondary infections. Finally, oral antihistamines are recommended for itching but have no effect on the activity of AD.

However, these therapies are not totally satisfactory. Indeed, most treatments offer only temporary and incomplete symptom relief. Moreover, long term use of topical corticosteroid is prone to side effects such as skin atrophy or thinning and topical calcineurin inhibitors can cause some local skin irritation or burning and itching sensations when treatment is started. These side effects can affect patient compliance or may fear parents. Finally, systemic and UV therapies should be used very cautiously and should be reserved for adults with severe cases.

There is so a need for new therapies with better efficiency and lower side effects for long term use, especially in younger children. It would be valuable to have a safe treatment easy to use, cosmetically acceptable and adapted to young children while improving the speed of lesion resolution and reducing the frequency of the therapy. It would also be desirable to have emollient easy to apply, not greasy with a longer protection. As previously indicated, the levels of AMP expression and secretion are low in AD skin that may explain the higher susceptibility of AD skin with infections especially by *S. aureus*.

Consequently, there is a need to increase the expression of AMPs in AD skin to protect the skin from colonization by different pathogens.

Hence, there is a need for topical compositions that are easy to handle under industrial conditions, that are safe and easy to administer and that allow preventing and/or treating atopic dermatitis, in particular by boosting the endogenous antimicrobial defenses.

SUMMARY OF THE INVENTION

In this context, the inventors have demonstrated that a composition comprising a lactic acid bacteria, preferably *Lactobacillus johnsonii* LA1 NCC 533 (deposit number CNCM I-1225), was efficient for treating and/or preventing atopic dermatitis. More particularly, the inventors have surprisingly demonstrated that a composition of the invention allowed boosting the AMP expression on the skin and was thus effective for treating and/or preventing AD. More surprisingly, the composition of the invention was effective in treating AD even for a not superinfected case.

The present invention provides herein a composition comprising at least one lactic acid bacteria in an acceptable carrier, for use in the treatment and/or prevention of a dermatological disease, preferably atopic dermatitis.

In a particular embodiment, said at least one lactic acid bacteria is selected in a group consisting of *Lactobacillus johnsonii, Lactobacillus reuteri, Lactobacillus rhamnosus, Lactobacillus paracasei, Lactobacillus casei, Bifidobacterium bifidum, Bifidobacterium breve, Bifidobacterium animalis, Bifidobacterium infantis, Bifidobacterium dolescentis*, and *Bifidobacterium pseudocatenulatum*, and more preferably selected in the group consisting of *Lactobacillus johnsonii, Lactobacillus reuteri, Lactobacillus rhamnosus, Lactobacillus paracasei*, and *Lactobacillus casei*. In a more preferred embodiment, said at least one lactic acid bacteria is *Lactobacillus johnsonii* LA1 NCC 533 (deposit number CNCM I-1225). In a further more preferred embodiment, *Lactobacillus johnsonii* LA1 NCC533 is used as a non-replicating form, particularly is rendered non-replicating by a heat treatment.

In a further particular embodiment, the composition comprises from 0.01 to 5%, preferably from 0.01 to 3%, more preferably from 0.01 to 1%, even more preferably from 0.03 to 1%, by weight of at least one lactic acid bacteria, relative to the total weight of the composition. More preferably, the composition of the invention comprises from 0.01 to 0.5%, preferably from 0.1 to 0.3%, more preferably 0.1 or 0.3% by weight of at least one lactic acid bacteria, relative to the total weight of the composition.

In a further particular embodiment, the acceptable carrier of the composition of the invention comprises solvents, emulsifiers, suspending agents, decomposers, binding agents, chelating agents, stabilizing agents, diluents, antioxidants, gelling agents, preservatives, moisturizer or emollient agents, lubricants absorption delaying agents, skin-penetrating agents, liposomes, coloring materials, odor absorbers, pigments, and a mixture thereof. In a preferred embodiment, the composition comprises a moisturizer and/or an emollient agent, more preferably in a proportion from 0.1 to 5%, 0.1 to 2%, 0.5 to 1%, even more preferably 0.5 or 1%, by weight, relative to the total weight of the composition.

In a further particular embodiment, the composition as disclosed herein is a topical composition, preferably a lotion, a wash or a spray.

A further object the invention is a composition as disclosed herein, for treating and/or preventing atopic dermatitis by boosting the endogenous antimicrobial defenses.

A further object of the invention is a method for treating and/or preventing atopic dermatitis comprising administering a composition comprising at least one lactic acid bacteria in an acceptable carrier, in a subject in need thereof, in particular thereby boosting the endogenous antimicrobial defenses.

A further object of the invention is a use of a composition as disclosed herein for the manufacture a drug for treating and/or preventing atopic dermatitis.

LEGEND TO THE FIGURES

FIG. 1: Effect of HT La1 in kinetics at 0.3% in water on the AMP gene expression using the RHE model. Results are expressed as fold induction for each selected gene (hDEFB1, hDEFB4A, hDEFB103, hS100A7, hS100A8, hS100A9, hPI3 and hRNase7) calculated using the values obtained with the vehicle control samples as reference (FI=1), and depending on time expressed as hours.

Figure 2:
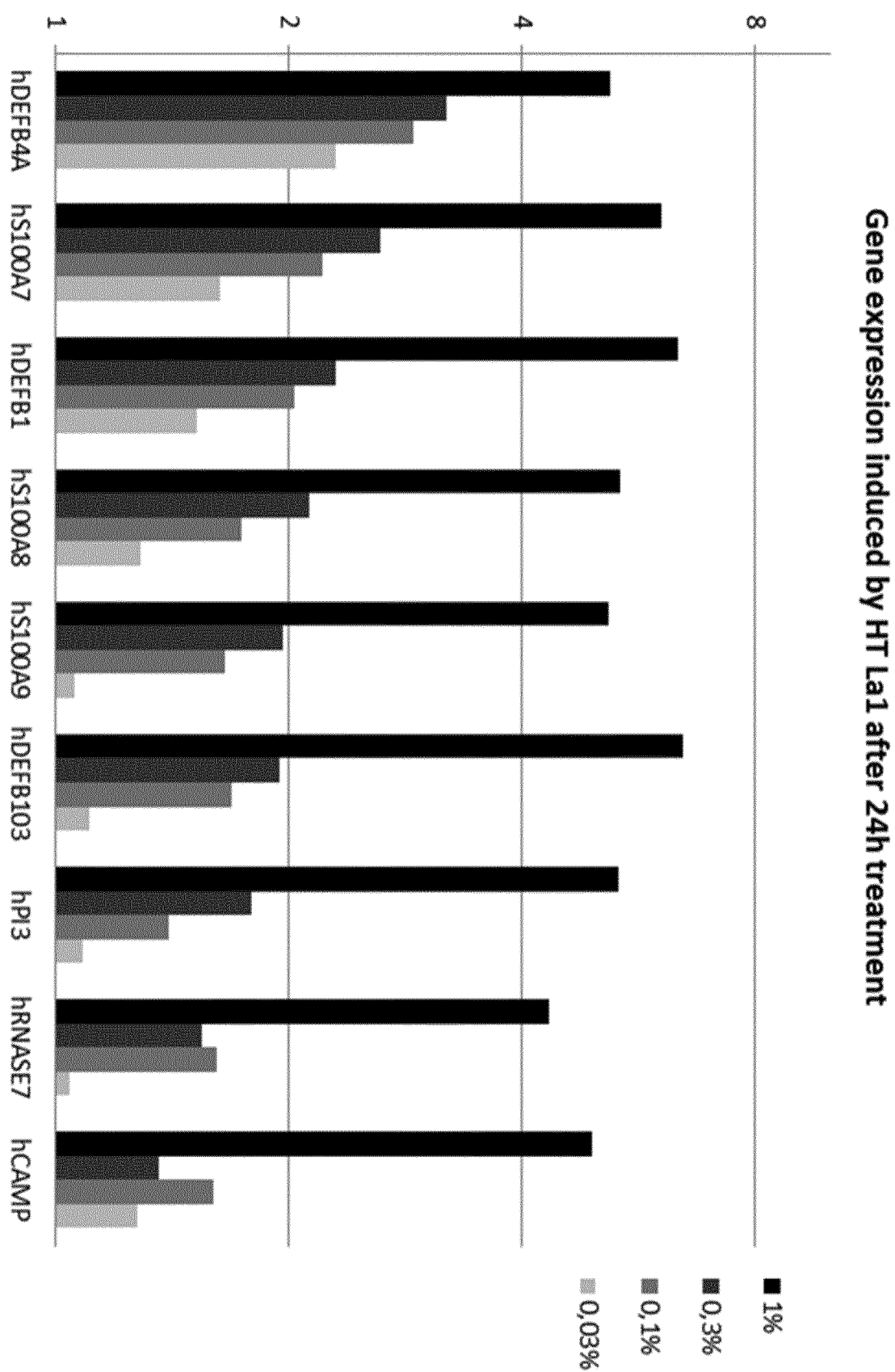

FIG. 2: Effect of HT La1 in dose response in water after 24 hours of treatment on AMP gene expression using the RHE model. Fold induction are calculated using the values obtained with the vehicle control samples after 24 hours of treatment as reference (FI=1).

Figure 3:
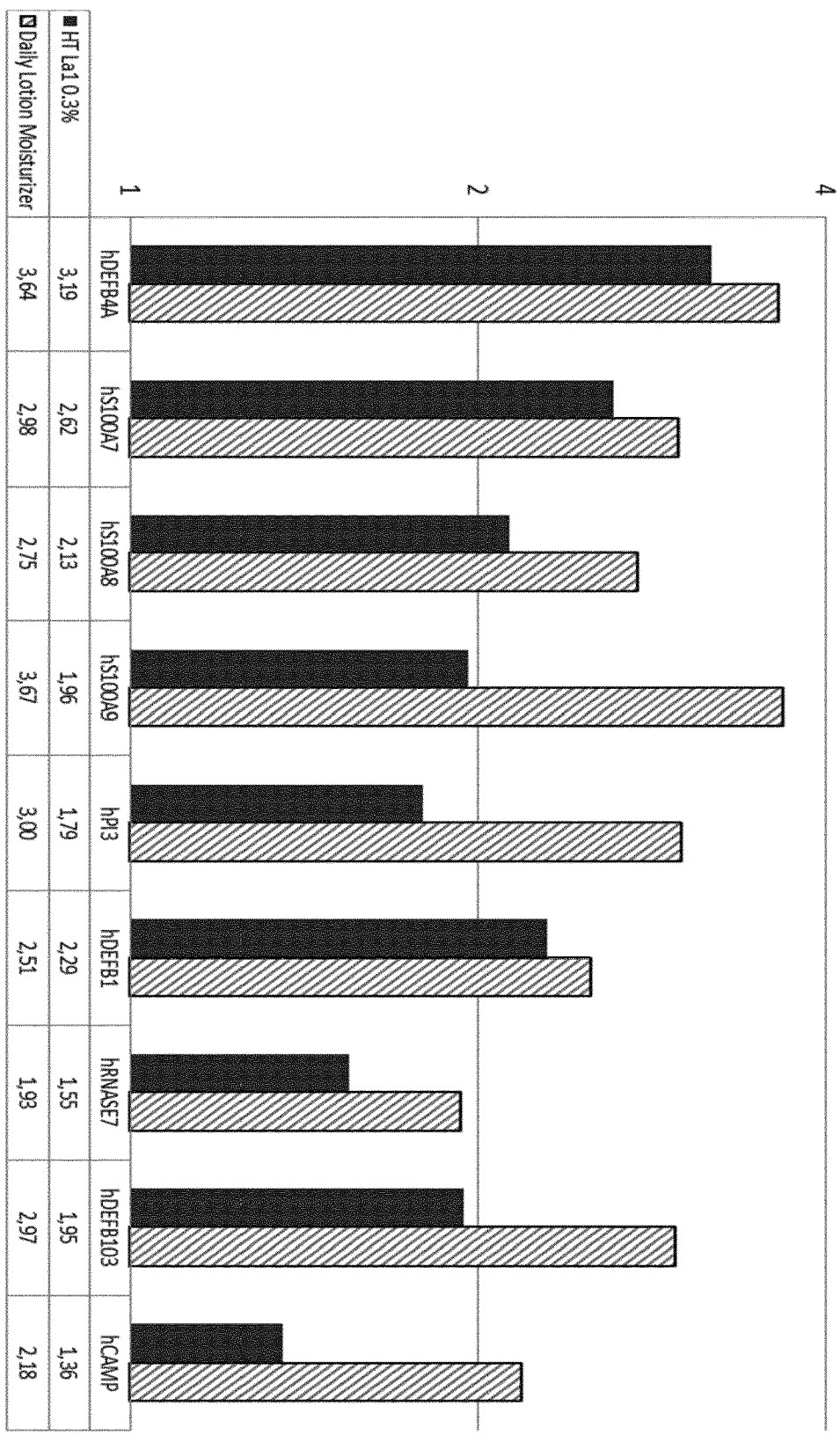

FIG. 3: Effect of HT La1 at 0.3% in water and in the daily moisturizer lotion according to example 4 after 24 hours treatment on AMP gene expression using the RHE model. Fold inductions are calculated using the values obtained with the respective vehicle control samples (water or the placebo according to example 4) after 24 hours of treatment as reference (FI=1).

Figure 4:
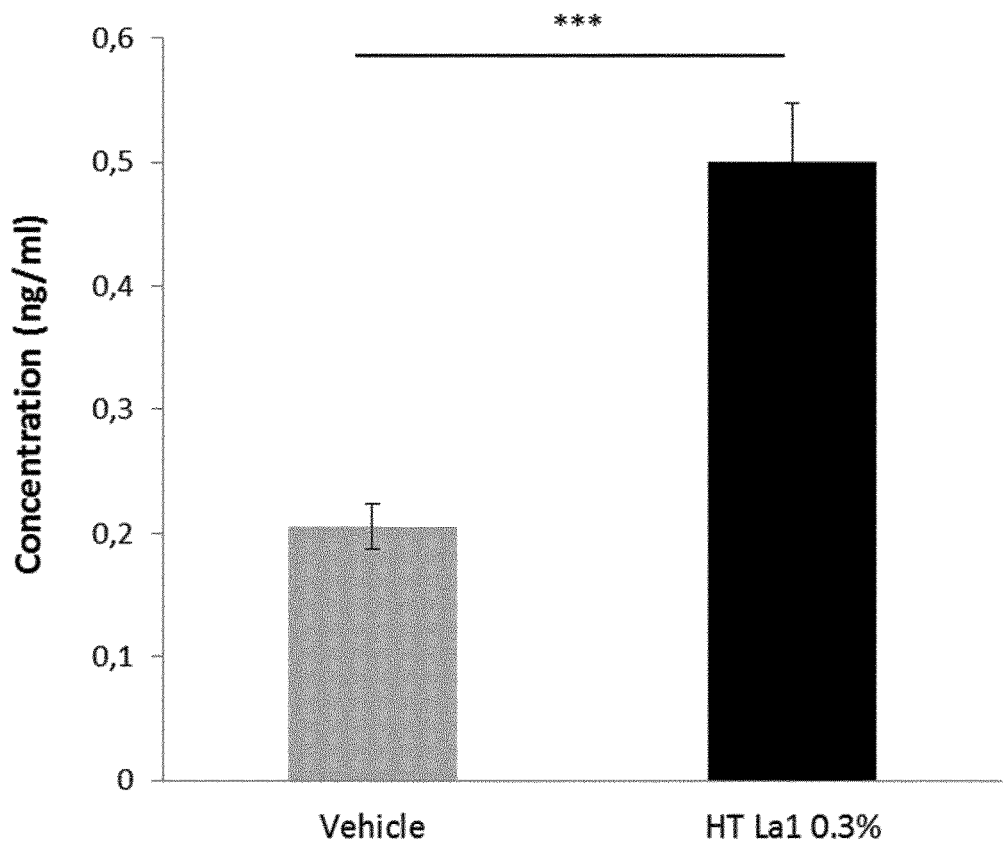

FIG. 4: Effect of HT La1 at 0.3% in water after 48 hours of treatment on the hβ2-defensin protein secretion in RHE sample supernatants. HT La1 at 0.3% in water was applied topically on RHE for 48 hours. The inter-group comparison was performed by Student's t-test. Threshold for statistical significance: p value<0.05=*, p value<0.01=, p value<0.001=*.

Figure 5:
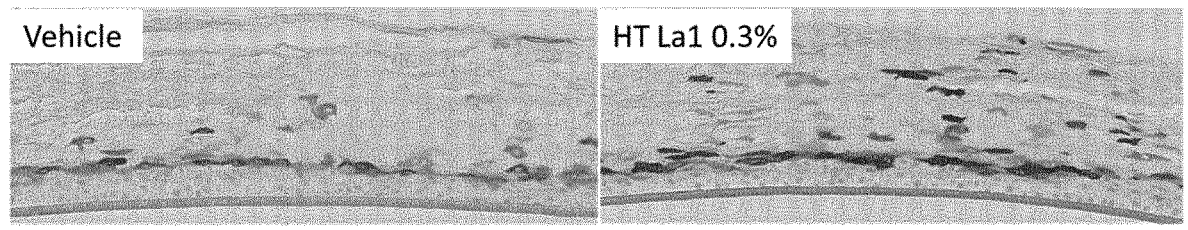

FIG. 5: Effect of HT La1 at 0.3% in water after 48 hours of treatment on the Psoriasin protein expression using the RHE model. HT La1 at 0.3% in water was applied topically on RHE samples for 48 hours. Topical treatment with water was performed as vehicle control.

Figure 6:
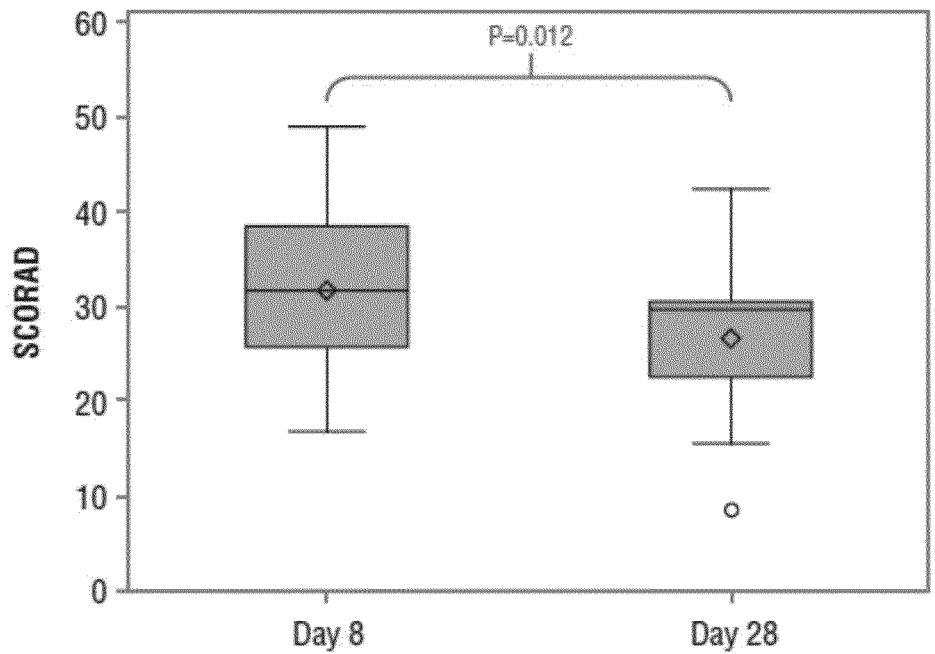

FIG. 6: SCORAD evolution of treated lesion for Population 2 with the composition of example 2.

Figure 7:
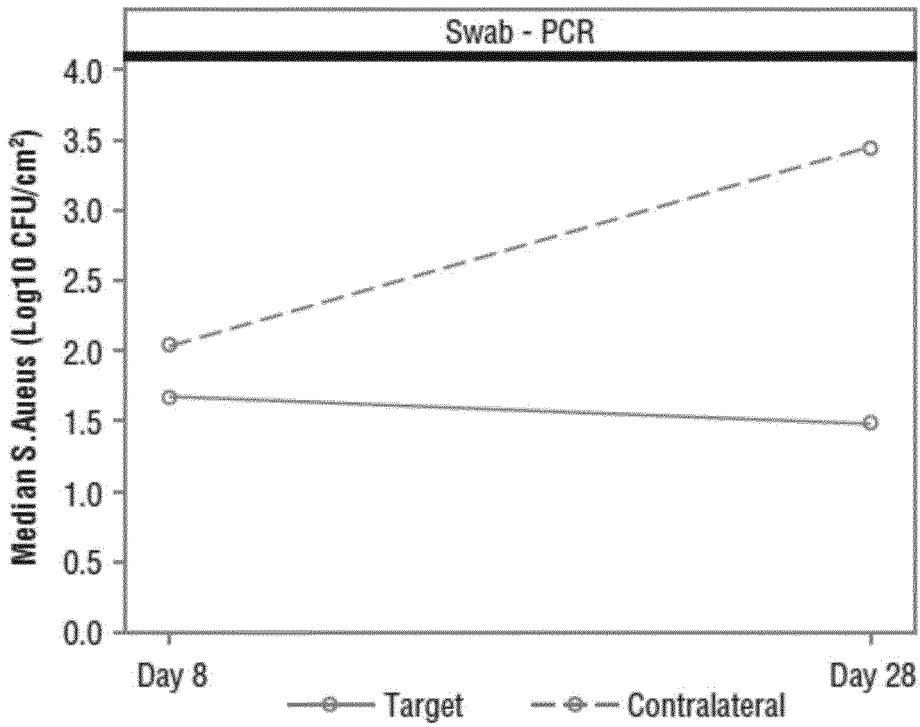

FIG. 7: SA load evolution of treated target vs contralateral lesion for population 2 with the composition of example 2.

DETAILED DESCRIPTION OF THE INVENTION

*L. johnsonii*, in particular non-replicating *L. johnsonii*, for example heat treated *L. johnsonii* LAI NCC 533 (deposit number CNCM I-1225) has shown superior effects on the induction of antimicrobial peptide expression than those previously identified and described in the previous literature.

Patent application WO2010/130662 from Nestec described, for example, that: *L. johnsonii* LAI NCC 533 strongly induces the constitutive hBD1 expression, and that Heat-treated *L. johnsonii* LAI NCC 533 up-regulates hBD1 more strongly than its live counterpart. As used herein, *Lactobacillus johnsonii* LA1 NCC533 is also called *Lactobacillus johnsonii* NMR LA1 and will be indifferently named in the present application LA1, HT LA1 or NMR LA1. *Lactobacillus johnsonii* LA1 NCC533 rendered non-replicating by a heat treatment can be named under the commercial name Heat-treated *Lactobacillus johnsonii* or HT LA1.

However, effects of *L. johnsonii* on expression of other antimicrobial peptides have never been demonstrated. Additionally, topical formulation that allows boosting the antimicrobial peptide expression on atopic dermatitis skin has never been described.

Surprisingly, the topical composition according to the invention is effective in maintaining the effect of HT LA1 on antimicrobial peptide and consequently in treating and preventing atopic dermatitis.

Therefore, a preferred embodiment concerns a composition comprising a lactic acid bacteria for use for the prevention and/or treatment of dermatological conditions, preferably for the prevention and/or treatment of atopic dermatitis (AD). Preferably, the lactic acid bacteria is HT LA1.

In another general aspect, embodiments of the present invention relate to a method of treating or preventing AD in a subject.

The method comprises topically administrating to a skin area of a subject a topical composition according to an embodiment of the present invention, wherein the skin area is, or prone to be, affected by AD.

The term "topical" as used herein refers to the administration of a composition to a particular spot on the outer surface of the body, including but not limited to the skin, scalp, mucous membranes and/or integuments.

The terms "composition" or "formulation" as used herein is intended to encompass a product comprising the specified ingredient in the specified amount, as well as any product which results, directly or indirectly, from combinations of the specified ingredient in the specified amount.

The terms "topical composition" or "topical formulation" as used herein mean any composition or formulation which is pharmaceutically and/or cosmetically acceptable for topical delivery of the specified compounds according to embodiments of the invention.

In one embodiment, "treatment" or "treating" refers to an amelioration, prophylaxis, or reversal of disease or disorder, or of at least one discernible symptom thereof. In another embodiment, "treatment" or "treating" refers to an amelioration, prophylaxis or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, compounds of interest are administered as a preventive measure. As used herein, "prevention" or "preventing" refers to a reduction or the risk of acquiring a given disease or disorder. In a preferred mode of embodiment, the specified compounds are administered as a preventive measure to a subject having a predisposition to a disease or disorder even though symptoms of the disease or disorder are absent or minimal. In one embodiment, predisposition to atopic dermatitis can be itching or pruritic skin, pruritus, atopic skin.

As used herein, the term "subject" means any animal, preferably a mammal, most preferably a human, to whom will be or has been administered compounds or topical formulations according to embodiment to the invention. The term "mammal" as used herein, encompasses any mammal. Example of mammals include, but are not limited to, cows, horse, sheep, pigs, cats, dogs, mice, rats, rabbits, guinea pigs, monkey, humans, etc., more preferably a human. The preferred subjects concerned by the present invention for the treatment and/or prevention of atopic dermatitis are a pregnant woman, a child or an infant. As used herein, a newborn baby is a baby from 0 to 28 days, an infant is a baby from 1 month to 2 years and a child is aged from 2 years to 14 years or from 2 years to the age of puberty. Preferably, a subject is in need of, or has been the object of observation or experiment of, treatment or prevention of AD and symptoms associated thereof.

As used herein, the term "dermatological conditions" or "dermatological disease" is intended to encompass any type of dermatological condition that is in need of treatment or prevention. Examples include, but are not limited to AD, eczema, xerosis, and more preferably AD.

As used herein, the term "therapeutically effective amount" refers to a sufficient quantity of drug to produce a desired therapeutic result. In the present case, this means that a sufficient amount of HT LA1. The effective amount may vary depending on the specific composition that is being used, and also depends on a variety of factors and conditions related to the patient being treated and the severity of the disorder. The determination of an effective amount or therapeutically effective amount of a given composition is well within the ability of those skilled in the art.

According to a preferred embodiment, the lactic acid bacteria of the composition of the invention is selected in a group consisting of *Lactobacillus johnsonii*, *Lactobacillus reuteri*, *Lactobacillus rhamnosus*, *Lactobacillus paracasei*, *Lactobacillus casei*, *Bifidobacterium bifidum*, *Bifidobacterium breve*, *Bifidobacterium animalis*, *Bifidobacterium infantis*, *Bifidobacterium dolescentis*, and *Bifidobacterium pseudocatenulatum*, and more preferably selected in the group consisting of *Lactobacillus johnsonii*, *Lactobacillus reuteri*, *Lactobacillus rhamnosus*, *Lactobacillus paracasei*, and *Lactobacillus casei*. In a preferred embodiment, the lactic acid bacteria is *Lactobacillus johnsonii*.

In a more preferred embodiment, the lactic acid bacteria is *L. johnsonii* LA1, NCC 533, deposit number CNCM I-1225. *Lactobacillus johnsonii* LA1 NCC533 (CNCM I-1225) was deposited, according to the Treaty of Budapest, at the Collection Nationale de Cultures de Microorganismes (CNCM) [National Collection of Microorganism Cultures], Institut Pasteur, 28 rue du Docteur Roux, 75724 Paris Cedex 15, France, on Jun. 30, 1992 under the reference CNCM I-1225.

The lactic acid bacteria can be a replicating or non-replicating bacteria. More preferably, the lactic acid bacteria is a non-replicating bacteria or an essentially non-replicating bacteria.

Non-replicating lactic acid bacteria, and in particular *L. johnsonii* LA1 NCC533 (deposit number CNCM I-1225) can be obtained by heat treatment. The non-replicating bacteria have the advantage of being even more effective than their alive counterpart. More particularly, the use of non-replicating microorganisms, such as heat-treated *L. johnsonii* LA1 NCC533, instead of their alive counterparts, has further the advantages of:
    reducing the potential risk of live probiotic-associated sepsis in the sensitive targeted populations,
    representing a safe alternative to immunocompromised patients, and lower processing hurdles, can be integrated in shelf stable liquid products with an long shelf life.

Heat inactivation may occur after a heat treatment at least about 70° C. and any kind of heat treatment can be used to inactivate the probiotic microorganisms such as *Lactobacillus johnsonii* LA1 NCC533 (CNCM I-1225). For example, the probiotic microorganisms such as *Lactobacillus johnsonii* LA1 NCC533 (CNCM I-1225) may be rendered non-replicating after a treatment at 110° C. to 140° C. for 1-30 seconds, e.g. 10-20 seconds.

Hence, in one embodiment of the present invention, at least 90%, for example at least 95% preferably at least 98%, most preferably at least 99%, ideally at least 99.9%, or all of the lactic acid bacteria, especially *L. johnsonii* LA1 NCC533, are in a non-replicating form. Advantageously, the composition should contain non-replicating bacteria and should be more effective than their live counterpart.

In one general aspect, the invention relates to a topical composition comprising a lactic acid bacteria, preferably Heat Treated *Lactobacillus Johnsonii* or HTLA1.

In specific compositions according to the invention, HT LA1 is used in an amount ranging from 0.01 to 5%, 0.01 to 3%, 0.01 to 1%, in particular from 0.03 to 1%, and more specifically in the amount of 0.03%, 0.1%, 0.3% and 1%, by weight with respect to the total weight of the composition.

In a more specific aspect, the pharmaceutical composition of the invention comprises an amount of the lactic acid bacteria, especially *Lactobacillus johnsonii* LA1 NCC533 (CNCM I-1225), corresponding to about $10^4$ to $10^{12}$ cfu/g.

The topical compositions of the invention can further comprise at least one additional active ingredient. The additional active agent is preferably selected from the group comprising, but not limited to, antibiotics, antibacterial agents, antiviral, antiparasitic, antifungal agents, anesthetics, analgesics, antiallergic agents, retinoids, free-radical scavengers, antipruriginous, antihistamines, immunosuppressant products, corticosteroids, keratolytic agents, intravenous immunoglobulin, anti-angiogenic, anti-inflammatory and/or a mixture thereof.

The topical compositions of the invention can additionally comprise any pharmaceutically acceptable carrier known in the art for topically administering pharmaceuticals. For instance, the carrier may include, but is not limited to, one or more of the following agents: solvents, emulsifiers, suspending agents, decomposers, binding agents, chelating agents, stabilizing agents, diluents, antioxidants, gelling agents, preservatives, moisturizer or emollient agents, lubricants, absorption delaying agents, skin-penetrating agents, liposomes, coloring materials, odor absorbers or pigments and a mixture thereof. In a preferred embodiment, according to the disease to be treated in the present invention, man skilled in the art may include at least one moisturizer or emollient agent to keep the skin moist and supple, by reducing water loss from the epidermis. For instance, the moisturizer or emollient agent is panthenol, glycerin or mixture thereof.

The amounts and nature of the different constituents of the compositions according to the invention are those conventionally used in the field under considerations.

For instance, a preferred composition of the invention comprises from 0.01 to 5%, preferably from 0.01 to 3%, more preferably from 0.01 to 1%, even more preferably from 0.03 to 1%, or 0.03%, 0.1%, 0.3% or 1% by weight of at least one lactic acid bacteria, relative to the total weight of the composition. A more preferred composition of the invention comprises at least one lactic acid bacteria in a proportion by weight as above defined, and a moisturizer agent in a proportion from 0.1 to 5%, preferably from 0.1 to 2%, more preferably from 0.5 to 1%, even more preferably 0.5 or 1% by weight relative, to the total weight of the composition.

As used herein, "pharmaceutically acceptable" means active agents, inert ingredients, or composition that are suitable for topical administration without undue toxicity, incompatibility, instability, irritation, allergic response, and the like, commensurate with a reasonable benefit/risk ratio.

The compositions of the invention can be provided in all pharmaceutical dosage forms normally used for a topical application including, but is not limited to solutions, emulsions, aerosol and non-aerosol sprays, creams, gels, powders, mousses, lotions, sticks, ointments, pastes, foam, creams, shampoos, body washes or face washes. These compositions are prepared according to usual methods. In a preferred embodiment, the composition of the invention is a lotion, a wash or a spray.

The pH of the topical formulations of the invention is preferably within a physiologically acceptable pH, e.g., within a range of about 5 to about 7, preferably within the range of about 5 to 6.

The invention also relates to a topical composition comprising HT LA1 for a use in the treatment and/or prevention of a dermatological condition, preferably atopic dermatitis (AD).

The invention also relates to the topical use of HT LA1 for the preparation of a medicament for the prevention and/or treatment of a skin condition, more preferably AD. The present invention also relates to a method of treating a dermatological condition, such as AD. The method comprises topically administering to the skin of the subject in need of the treatment a therapeutically effective amount of a topical composition comprising HT LA1.

Methods of the present invention can be used in conjunction with one or more other treatments and medications for the skin condition.

The other medicament or treatment can be administered to the subject simultaneously with, or in a sequence and within a time interval of, the administration of the topical composition, such that the active ingredients or agents can act together to treat or prevent AD and symptoms associated therewith. For example, the other medicament or treatment can be administered in the same or separate formulations at the same or different times. Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation. Preferably, the composition according to the invention is administered by topical route.

In a particular embodiment, the compositions as disclosed herein can be administered from 1 week to 6 months, preferably from 2 weeks to 4 months, and can be renewed several times with or without a time delay. In a preferred embodiment, the composition according to the invention is administered once a day or twice a day. More preferably, the composition is administered once a day.

This invention will be better understood by reference to the non-limiting examples that follow, but those skilled in the art will readily appreciate that the examples are only illustrative of the invention as described more fully in the claims which follow thereafter.

EXAMPLES

Example 1

Composition of Hair, Face and Body Wash According to the Invention

| COMMERCIAL NAME | INCI NAME | % w/w | % w/w |
|---|---|---|---|
| PLANTACARE 818UP | Coco glucoside | 9.00 | 9.00 |
| PROTELAN LS9011 | Sodium Lauroyl sarcosinate | 8.00 | 8.00 |
| PROTELAN AG 818 G | Sodium Cocoyl Glutamate | 10.00 | 10.00 |
| KELTROL CG-SFT | Xanthan Gum | 0.40 | 0.40 |
| NATROSOL PLUS 330CS | Cetyl Hydroxyethylcellulose | 1.20 | 1.20 |
| PROBENZ SP | Sodium Benzoate | 0.20 | / |
| ZEMEA | 1,3-Propanediol | 5.00 | 5.00 |
| GLYCERINE 4810 VEGETABLE | Glycerin | 3.00 | 3.00 |
| STEPAN MILD GCC | Glyceryl caprylate/caprate | 1.00 | 1.00 |
| D-PANTHENOL USP | Panthenol | 0.50 | 0.50 |
| PRESTIGE SUPER SOFT SILVER | Mica/Titanium dioxide | 0.10 | 0.10 |
| ACIDE CITRIQUE MONOHYDRATE | Citric acid | 1.00 | 1.00 |
| Heat Treated *Lactobacillus Johnsonii* | Uncommunicated | 0.10 | 0.10 |
| EAU PURIFIEE | Water | Qsp 100 | Qsp 100 |
| HYDROLITE 5/5P | Pentylene Glycol | / | 3.00 |

Example 2

Composition of Daily Moisturizer Lotion According to the Invention

| COMMERCIAL NAME | INCI NAME | Composition with LA1 % w/w | Placebo % w/w |
|---|---|---|---|
| SATIAXANE UCX 911 | Xanthan Gum | 0.70 | 0.70 |
| GLYCERINE 4810 VEGETALE | Glycerin | 3.00 | 3.00 |
| ZEMEA | Propanediol | 4.00 | 4.00 |
| D-PANTHENOL USP | Panthenol | 0.50 | 0.50 |
| CERALUTION H | Behenyl alcohol/glyceryl stearate/glyceryl stearate citrate/na dicocoylethylenediamine PEG-15 sulfate | 3.00 | 3.00 |
| EMULGADE 1000NI | Cetearyl alcohol and ceteareth-20 | 2.00 | 2.00 |
| HUILE DE TOURNESOL OLEIQUE BIO | Sunflower (*helianthus annuus*) seed oil | 5.00 | 5.00 |
| LIPEX SHEA SOFT | Butyrospermum Parkii | 2.00 | 2.00 |
| MIGLYOL 812N | Caprylic/Capric Triglyceride | 4.00 | 4.00 |
| CETIOL CC | Dicaprylyl carbonate | 5.00 | 5.00 |
| LANETTE 16 | Cetyl alcohol | 2.00 | 2.00 |
| HYDROLITE CG | Caprylyl Glycol | 0.35 | 0.35 |
| Heat Treated *Lactobacillus johnsonii* | Uncommunicated | 0.30 | / |
| TITRIPLEX III | Disodium EDTA | 0.10 | 0.10 |
| SODIUM HYDROXIDE (10% Aqueous solution) | Sodium hydroxide | Qs pH 5-5.5 | Qs pH 5-5.5 |
| EAU PURIFIEE | Water | Qsp 100 | Qsp 100 |

Example 3

Composition of Daily Moisturizer Lotion According to the Invention

| COMMERCIAL NAME | INCI NAME | Composition with LA1 % w/w | Placebo % w/w |
|---|---|---|---|
| SATIAXANE UCX 911 | Xanthan Gum | 0.70 | 0.70 |
| GLYCERINE 4810 VEGETALE | Glycerin | 3.00 | 3.00 |
| ZEMEA | Propanediol | 5.00 | 5.00 |
| D-PANTHENOL USP | Panthenol | 0.50 | 0.50 |

-continued

| COMMERCIAL NAME | INCI NAME | Composition with LA1 % w/w | Placebo % w/w |
|---|---|---|---|
| CERALUTION H | Behenyl alcohol/glyceryl stearate/glyceryl stearate citrate/na dicocoylethylenediamine PEG-15 sulfate | 3.00 | 3.00 |
| EMULGADE 1000NI | Cetearyl alcohol and ceteareth-20 | 2.00 | 2.00 |
| HUILE DE TOURNESOL OLEIQUE BIO | Sunflower (*helianthus annuus*) seed oil | 5.00 | 5.00 |
| LIPEX SHEA SOFT | Butyrospermum Parkii | 2.00 | 2.00 |
| MIGLYOL 812N | Caprylic/Capric Triglyceride | 4.00 | 4.00 |
| CETIOL CC | Dicaprylyl carbonate | 5.00 | 5.00 |
| LANETTE 16 | Cetyl alcohol | 2.00 | 2.00 |
| HYDROLITE CG | Caprylyl Glycol | 0.60 | 0.60 |
| Heat Treated *Lactobacillus johnsonii* | Uncommunicated | 0.30 | / |
| TITRIPLEX III | Disodium EDTA | 0.10 | 0.10 |
| SODIUM HYDROXIDE (10% Aqueous solution) | Sodium hydroxide | Qs pH 5-5.5 | Qs pH 5-5.5 |
| EAU PURIFIEE | Water | Qsp 100 | Qsp 100 |

Example 4

Composition of Daily Moisturizer Lotion According to the Invention

| COMMERCIAL NAME | INCI NAME | composition with LA1 % w/w | Placebo % w/w |
|---|---|---|---|
| KELTROL CG-SFT | Xanthan Gum | 0.70 | 0.70 |
| GLYCERINE 4810 VEGETALE | Glycerin | 3.00 | 3.00 |
| ZEMEA | Propanediol | 7.00 | 7.00 |
| PROLIX RB | Polyglyceryl-3 rice branate | 4.00 | 4.00 |
| LIPACIDE C8G | Capryloyl Glycine | 1.00 | 1.00 |
| HUILE DE TOURNESOL OLEIQUE DESODORISEE BIO | Sunflower (*helianthus annuus*) seed oil | 5.00 | 5.00 |
| ACTICIRE | Jojoba Esters (and) *Acacia Decurrens* Flower Wax (and) *Helianthus Annuus* (Sunflower) Seed Wax (and) Polyglycerin-3 | 5.00 | 5.00 |
| ISOSTERATE D'ISOSTEARYLE | Isosterate isostearyle | 5.00 | 5.00 |
| CETIOL CC | Dicaprylyl carbonate | 5.00 | 5.00 |
| LIPOCIRE A | C10-18 triglycerides | 3.00 | 3.00 |
| DERMOSOFT 688 | p-anisic acid | 0.10 | 0.10 |
| D-PANTHENOL USP | Panthenol | 1.00 | 1.00 |
| Heat Treated *Lactobacillus johnsonii* | Uncommunicated | 0.30 | / |
| SODIUM HYDROXIDE (10% Aqueous solution) | Sodium hydroxide | Qs pH 5-5.5 | Qs pH 5-5.5 |
| EAU PURIFIEE | Water | Qsp 100 | Qsp 100 |

Example 5

Composition of Daily Moisturizer Lotion According to the Invention

| COMMERCIAL NAME | INCI NAME | Composition with LA1 % w/w | Placebo % w/w |
|---|---|---|---|
| KELTROL CG-T | Xanthan Gum | 0.20 | 0.20 |
| VIVAPUR COS5 | Microcrystalline Cellulose (and) Cellulose Gum | 2.00 | 2.00 |
| GLYCERINE 4810 VEGETALE | Glycerin | 3.00 | 3.00 |
| ZEMEA | Propanediol | 7.00 | 7.00 |
| EMULIUM KAPPA | Candelilla/Jojoba/Rice Bran Polyglyceryl-3 Esters (and) Glyceryl Stearate (and) Cetearyl Alcohol (and) Sodium Stearoyl Lactylate | 4.00 | 4.00 |
| LIPACIDE C8G | Capryloyl Glycine | 1.00 | 1.00 |
| LIPACIDE UG | Undecylenoyl glycine | 0.20 | 0.20 |
| HUILE DE TOURNESOL OLEIQUE DESODORISEE BIO | Sunflower (*helianthus annuus*) seed oil | 5.00 | 5.00 |
| ISOSTERATE D'ISOSTEARYLE | Isosterate isostearyle | 7.00 | 7.00 |
| CETIOL CC | Dicaprylyl carbonate | 3.00 | 3.00 |
| CUTINA HVG | Hydrogenated Vegetable Glycerides | 2.00 | 2.00 |
| D-PANTHENOL USP | Panthenol | 1.00 | 1.00 |
| Heat Treated *Lactobacillus johnsonii* | Uncommunicated | 0.30 | / |

-continued

| COMMERCIAL NAME | INCI NAME | Composition with LA1 % w/w | Placebo % w/w |
|---|---|---|---|
| SODIUM HYDROXIDE (10% Aqueous solution) | Sodium hydroxide | Qs pH 5-5.5 | Qs pH 5-5.5 |
| EAU PURIFIEE | Water | Qsp 100 | Qsp 100 |

Example 6

Evaluation of the Effect of HT La1 on Antimicrobial Peptide Expression

The aim of this study was to evaluate the effect of the HT La1 in kinetics and at different concentrations in water for one composition according to the invention (Example 4) on antimicrobial peptide expression in the reconstructed human epidermis model (RHE) using qRT-PCR, Elisa and immunohistochemistry methods.

Biological Model Used Are:
Epidermis: 17-day-old reconstructed human epidermis samples (RHE) in 24-well plate from SkinEthic (RHE/HTS).
Assay medium: SkinEthic Growth Medium
Culture conditions: 37° C., 5% CO2
The compound used was HT La1 provided to Galderma R&D by Nestlé PTC. HT La1 suspensions at each concentration (w/w) in sterile distilled water (RNAse/DNase free) were prepared extemporary from the powder (Initial concentration=$3.1*10^{11}$ cfu/g) and kept under constant stirring at room temperature until and during use.

One formulation concept (Daily moisturizer lotion according to example 4) and respective placebo were supplied by the formulation unit of Galderma R&D Full-Development department.

Treatments were Performed with the Following Protocol:
Treatments were performed using reconstructed human epidermis samples from SkinEthic. RHE samples were topically treated by HT La1 at different concentrations in water (50 µl) under constant stirring. Topical treatment with water (50 µl) was performed in parallel (vehicle control condition).

Formulation concept and placebo (according to examples 4) were applied to RHE samples by topical route (3 µl) using Microman M10 pipette.

After 4, 8, 16, 24 and 48 hours of treatment, RHE samples were collected for gene expression and histological analysis. Supernatants were collected and stored at −80° C. for future analysis (AMP secretion). All experimental conditions were performed in replicates (n=3 or 4).

Gene Expression was Analyzed with the Following Protocol:
RHE samples were first crushed using Tissue ruptor (Qiagen), and then homogenates were treated with Proteinase K for 20 minutes. Then total RNA was extracted using the Hamilton automat platform using the RNAdvanced Tissue Kit (ref. A32646) from Agencourt following supplier recommendations. Total RNA were eluted in 40 µL of RNase-DNase free water and stored at −80° C. until quantification with Nanodrop 8000.

For each sample, reverse transcription was performed from 300 ng of total RNA using High capacity cDNA Reverse Transcription kit from Applied Biosystems (ref. 4368813). Real time PCR was performed using Universal PCR Master Mix from Applied Biosystems (Ref 4324018) using cDNA diluted at 2.5 with RNase-DNase free water.

The list of genes evaluated using qRT-PCR is reported in the table below:

| Gene name | Gene symbol | Assay ID (Applied Biosystems) |
|---|---|---|
| human β-defensin-1 (hBD-1) | hDEFB1 | Hs00608345_m1 |
| human β-defensin-3 (hBD-3) | hDEFB103 | Hs04194486_g1 |
| human β-defensin-2 (hBD-2) | hDEFB4A | Hs00823638_m1 |
| cathelicidin antimicrobial peptide (LL-37 precursor) | hCAMP | Hs00189038_m1 |
| S100 calcium binding protein A7 (Psoriasin) | hS100A7 | Hs00161488_m1 |
| S100 calcium binding protein A8 (calgranulin A) | hS100A8 | Hs00374264_g1 |
| S100 calcium binding protein A9 (calgranulin B) | hS100A9 | Hs00610058_m1 |
| peptidase inhibitor 3, skin-derived/ Elafin/SKALP | hPI3 | Hs00160066_m1 |
| RNase 7 | hRNASE7 | Hs00922963_s1 |
| glyceraldehyde-3-phosphate dehydrogenase | hGAPDH | PDAR 4326317E |

Normalised Ct was determined from raw data using Excel. "Undetermined" Ct values were arbitrary fixed at 40 in order to calculate representative normalised Ct value:

Normalised $Ct$=[$Ct$ target−$Ct$ mean HKG of sample]+mean $Ct$ HKG study

Then the fold induction of each gene was calculated using normalised Ct of control samples at each time of treatment:

Fold Induction (FI)=2−(Normalised $Ct$ treated sample−Normalised $Ct$ water or placebo control)

Protein Expression was Evaluated with the Following Protocols:
Human β2-defensin secretion was quantified in the RHE sample supernatant using the Human BD-2 ELISA Development Kit (Peprotech ref 900-K172) following the manufacturer recommendation.

Psoriasin expression was studied using immunohistochemistry. In order to perform a histological analysis, RHE samples were collected at the end of incubation, rinsed and fixed with formaldehyde solution. The sections were deparaffinised then the antigenic sites were retrieved with pH6 retrieval solution. The sections were washed and incubated with hydrogen peroxide. The sections, once washed, were incubated in a blocking solution and then incubated with the primary antibody (anti-psoriasin). After washing, the labelling was revealed using a detection kit in peroxidase and nuclei were counter-stained with a solution of haematoxylin. The sections were washed in ultrapure water and mounted in aqueous medium. Sections were observed and scanned using the Nanozoomer scanner (Hamamatsu).

Effect of HT La1 at 0.3% in Water on AMP Gene Expression

The effect of HT La1 by topical application at 0.3% in water was firstly evaluated in kinetics on AMP gene expression using the RHE model (FIG. 1).

As observed in FIG. 1 representing the expression of each modulated gene depending on time:

(1) hDEFB4A expression was induced after 16 hours of treatment with HT La1 at 0.3% in water with a FI mean=4 compared to the vehicle control sample.

(2) hDEFB1 and hS100A7 expression was induced after 24 hours of treatment with HT La1 at 0.3% in water with a similar FI mean ≥2 compared to the vehicle control sample.

(3) hDEFB103, hS100A8 and hS100A9 expression is induced only after 48 hours of treatment with HT La1 at 0.3% in water with a FI mean ≥2 compared to the vehicle control sample.

The expression of hPI3, hRNASE7 and hCAMP were slightly induced (FI< or=2) after 48 hours of treatment with HT La1 at 0.3% in water.

HT La1 at 0.3% in water was able to induce the expression of the 9 AMP gene studied with different profiles depending on time. Most of the genes were induced after 24 h of treatment.

Therefore, the effect of HT La1 on the AMP gene expression was secondly evaluated in dose-response range from 0.03% to 1% in water after 24 hours of treatment.

As shown in FIG. 2, HT La1 was able to induce the expression of all AMP genes in a dose-dependent manner with a maximum effect at 1% in water. At 1%, the expression of all AMP genes was induced with at least a fold induction >4 compared to the vehicle control sample.

Effect of the Formulation Concept with HT La1 at 0.3% on AMP Gene Expression

The effect of the formulation concept corresponding to the daily moisturizer lotion according to Example 4 with HT La1 at 0.3% was evaluated after 24 hours of treatment by topical application on AMP gene expression using the RHE model.

As shown in FIG. 3, the daily moisturizer lotion (according to example 4) after 24 hours of treatment was able to induce the expression of all antimicrobial peptide genes evaluated with a fold induction >2. The induction profile appears better with HT La1 at 0.3% in the daily moisturizer lotion compared to that observed with HT La1 at 0.3% in water. The expression of both genes encoding hDEFB4 A and hS100A9 was the most induced by the treatment with HT LA1 at 0.3% in the daily moisturizer lotion with a fold induction egual to 3.6.

Effect of HT La1 at 0.3% in Water on AMP Protein Secretion

The effect of HT La1 at 0.3% in water was investigated on hBD2 protein secretion after 48 hours of treatment using ELISA method.

As shown in FIG. 4, HT La1 topically applied in water at 0.3% induced the expression of hBD-2 protein expression after 48 h of treatment.

As shown in FIG. 5, HT La1 topically applied in water at 0.3% induced the expression of Psoriasin protein after 48 h of treatment.

Based on these results, the inventors have confirmed that non-replicating microorganism LA1 (HT La1) was able to induce endogenous antimicrobial defenses of the epidermis. These results illustrate the effect on "endogenous antimicrobial defense boosting" for the compositions for use of the invention for treating and/or preventing atopic dermatitis.

Example 7

Effect of the Composition of Example 2 on *Staphylococcus Aureus* (SA) Colonization in Atopic Dermatitis (AD)

Material and Methods

AD patients were enrolled in an open-label multicentric study.

In a first part, microbiological samples were taken at target and contralateral lesions at days D1, D3 and D8 using scrub-wash (Williamson and Kligman,1965) or nylon flocked swab (Eswab 480 CE, Copan). SA load was quantified by real-time PCR (Xpert SA Nasal Complete, Cepheid) and by culture on selective chromogenic medium (BBL Chromagar *Staph Aureus*, BectonDickinson) (Verhoeven et al., 2012). Repeatability and reproducibility of all 4 couples of methods were evaluated to select the best couple.

In a second part, patients with a visible clinical target lesion colonized by SA were treated by composition of example 2 from D8 to D28. Contralateral lesion was treated as the subject was used to. Microbiological samples were taken on the target treated and contralateral lesions at D8 and D18 using the selected couple of methods. Modified SCORAD of the treated lesion was recorded for efficacy assessment.

Results

A total of 31 subjects (15 males) with mild (n=2, 6.5%), moderate (n=25, 80.6%) and severe (n=4, 12.9%) AD were enrolled at D1 (Population 1). At D8, 21 subjects (14 males) with moderate (n=18, 85.7%) and severe (n=3, 14.3%) AD were eligible for treatment (Population 2). No statistically difference was found between the two populations.

1. Part 1: Evaluation of Sampling and Quantification Methods

At D1, 71% AD subjects were SA carrier with a mean bacterial load ranging from 2.6 to 3.4 Log 10 CFU/cm$^2$ according to the couple of methods.

All combinations yielded a good repeatability (R>0.83, p<0.001 between first and second sampling) and reproducibility (no time effect between D1 and D3) with a high correlation between qPCR and culture (R=0.92, p<0.001). Accordingly, the combination of swab and qPCR was selected to test the product effect.

2. Part 2: Evaluation of the Composition of the Invention According to Example 2

The treatment with composition of example 2 produced a statistically significant SCORAD decreased on the treated target lesion between D8 (32.2±7.0) and D28 (26.2±7.9) by −4.93±8.23 (p=0.012) (FIG. 6).

Comparing to the contralateral lesion, the composition of example 2 was found to control the SA load of the treated target lesion after three weeks of treatment (−1 Log 10(CFU/cm$^2$), P<0.05) (FIG. 7). Interestingly, the highest SA skin load was a predictive factor of the microbiological response. (OR=3.1 95% CI [1.02–9.55], $X^2$ test p<0.05). The treatment with composition according to the invention was shown to be safe and effective in reducing SCORAD after 21 days of treatment.

CONCLUSIONS

The 21-day daily moisturizer lotion treatment of the target lesion resulted in a statistically significant decrease in SCORAD from Baseline and Day 8 to Day 28 (p-values of 0.005 and 0.012, respectively). This study demonstrated that the composition comprising the non-replicating microorganism LA1 induced after three weeks a clinical improvement of AD lesions associated with a control of SA colonization of the lesional skin. These results are consistent with the fact that a high SA skin load was associated with a good microbiological response.

The invention claimed is:

1. A method of increasing antimicrobial peptide expression in atopic dermatitis skin, the method comprising topically administering, to the skin of an individual subject in need thereof, an effective amount of a pharmaceutical composition comprising:

(i) 0.1% to 3% by weight, relative to the total weight of the pharmaceutical composition, of a non-replicating *Lactobacillus johnsonii* LA1 NCC533 (deposit number CNCM I-1225); and (ii) 0.1% to 5% by weight, relative to the total weight of the composition, of a moisturizer and/or emollient;

wherein the *Lactobacillus johnsonii* LA1 NCC533 has been rendered non-replicating by heat treatment; and wherein, after 21 days of daily administration of said pharmaceutical composition, SCORing Atopic Dermatitis (SCORAD) for the treated skin is reduced, relative to untreated skin in the subject.

2. The method according to claim 1, wherein the pharmaceutical composition further comprises at least one ingredient selected from solvents, emulsifiers, suspending agents, decomposers, binding agents, chelating agents, stabilizing agents, diluents, antioxidants, gelling agents, preservatives, lubricants, absorption delaying agents, skin-penetrating agents, liposomes, coloring materials, odor absorbers, pigments, and a mixture thereof.

3. The method according to claim 1, wherein the pharmaceutical composition is formulated as a lotion, a wash or a spray.

4. The method according to claim 1 wherein the non-replicating *Lactobacillus johnsonii* LA1 NCC533 is present at a concentration of 0.1% or 0.3% by weight, relative to the total weight of the pharmaceutical composition.

5. The method according to claim 1, wherein the moisturizer and/or emollient is present at a concentration of 0.1% to 2% by weight, relative to the total weight of the pharmaceutical composition.

6. The method according to claim 1, wherein the moisturizer and/or emollient is present at a concentration of 0.5% to 1% by weight, relative to the total weight of the pharmaceutical composition.

7. The method according to claim 1, wherein the moisturizer and/or emollient agent is present at a concentration of 0.5% or 1% by weight, relative to the total weight of the pharmaceutical composition.

8. The method of claim 1, wherein skin load of *Staphylococcus aureus* in the subject is reduced after 21 days of daily administration, relative to untreated skin.

* * * * *